United States Patent [19]

Goudie

[11] 4,194,010

[45] Mar. 18, 1980

[54] PHARMACOLOGICALLY ACTIVE ENOL ETHER COMPOUNDS

[75] Inventor: Alexander C. Goudie, Harlow, England

[73] Assignee: Beecham Group Limited, United Kingdom

[21] Appl. No.: 911,797

[22] Filed: Jun. 2, 1978

Related U.S. Application Data

[62] Division of Ser. No. 735,738, Oct. 26, 1977.

[30] Foreign Application Priority Data

Oct. 29, 1975 [GB] United Kingdom ............ 44530/75

[51] Int. Cl.² ............... C07C 43/20; A61K 31/075
[52] U.S. Cl. .................................... 424/341; 568/633;
560/255; 260/340.7; 260/340.9 R; 424/311; 424/278
[58] Field of Search ............. 260/613 D; 568/633; 424/341

[56] References Cited

U.S. PATENT DOCUMENTS

| 3,626,012 | 12/1971 | Fried et al. | 260/613 D X |
| 3,641,161 | 2/1972 | Fried et al. | 260/613 D |
| 3,651,148 | 3/1972 | Nelson | 260/613 D X |
| 3,943,257 | 3/1976 | Anderson et al. | 260/613 R X |
| 3,969,415 | 7/1976 | Galantay | 260/613 D |

*Primary Examiner*—Bernard Helfin
*Attorney, Agent, or Firm*—Jacobs & Jacobs

[57] ABSTRACT

Acetals, enol acylates and enol ethers of the compound of the compound of the formula (I):

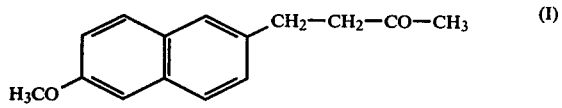

notionally derivable from a $C_{1-8}$ alcohol or $C_{1-8}$ acid are useful anti-inflammatory agents.

12 Claims, No Drawings

PHARMACOLOGICALLY ACTIVE ENOL ETHER COMPOUNDS

CROSS-REFERENCE

This is a division of Ser. No. 735,738 filed Oct. 26, 1977.

The present invention relates to naphthalene derivatives, to pharmaceutical compositions containing them and to the process for their preparation.

The present invention provides anti-inflammatory acetals, enol acylates and enol ethers of the compound of the formula (I):

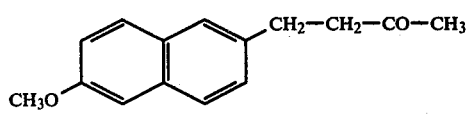

The compound of the formula (I) is described in Belgian Pat. No. 819794.

Suitably the aforementioned derivatives of the compounds of formula (I) are those notionally derivable from $C_{1-8}$ alcohols or $C_{1-8}$ acids.

Most suitably the aforementioned derivatives of the compounds of the formula (I) are those notionally derivable from $C_{2-4}$ alcohols or $C_{2-4}$ acids.

Particularly suitable compounds of this invention include those of the formulae (II)–(IV):

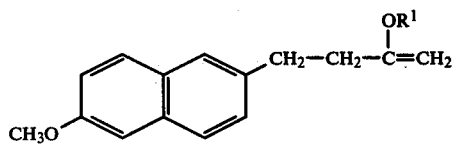

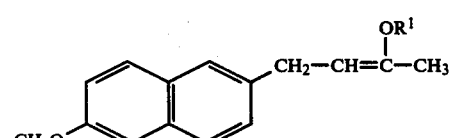

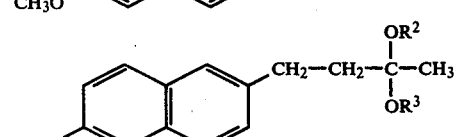

wherein $R^1$ is an ethyl, propyl, acetyl or propionyl group; $R^2$ is an ethyl or propyl group and $R^3$ is an ethyl or propyl group or is joined to $R^2$ so that $R^2$ together with $R^3$ is a $CH_2CH_2$ or $CH_2CH_2CH_2$ group.

The present invention also provides pharmaceutical compositions adapted for oral administration which comprise an anti-inflammatory compound of the invention together with a pharmaceutically acceptable carrier.

The compositions of this invention may be in the form of tablets, capsules, solutions, suspensions, granules or the like or any other dosage form conventionally used for the oral administration of anti-inflammatory agents. Such compositions may be prepared by conventional methods of formulation.

Generally such compositions will contain 50–1000 mgs of a compound of this invention and may be taken 1–6 times daily so that the daily dose is from 200 mg to 2000 mg.

The compounds of this invention are substantially non-toxic as is shown by their $LD_{50}$ values in mice which are greater than 1g/kg/orally. The compounds of this invention show activity on standard anti-inflammatory tests such as the Cotton Pellet Granuloma Test and Carageenin Induced Oedema Test at doses in the order of 50–200 mg/kg/orally.

The present invention also provides a process for the preparation of the compounds of this invention which process comprises the acetalation, enol acylation or enol etherification of the compound of the formula (I):

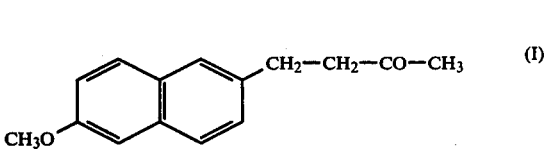

Such reactions may be brought about under conventional reaction conditions such as reaction with an alcohol under slow dehydrating conditions, reaction with an orthoester such as an orthoformate, reaction with an isopropenyl ester and the like.

Such reactions will normally take place in an inert solvent such as benzene or toluene at an elevated temperature, for example at the reflux point of the mixture.

It is frequently beneficial to include a dehydration catalyst such as p-toluenesulphonic acid in the mixture.

The following Examples illustrate the invention:

EXAMPLE 1

4-(6'-Methoxy-2'-naphthyl)-2-ethylenedioxybutane

A solution of 4-(6'-methoxy-2'-naphthyl)butan-2-one (5 g), ethylene glycol (30 ml) and p-toluenesulphonic acid (0.2 g) in benzene (250 ml) was refluxed for 20 hours with constant separation of water (Dean-Stark trap). The mixture was cooled to room temperature, basified with dilue sodium bicarbonate solution (60 ml) and extracted with ether (3×100 ml). The combined organic fraction was washed with water (2×50 ml), dried and concentrated. Recrystallisation of the crude solid from 40°-60° petrol gave pure 4-(6'-methoxy-2'-naphthyl)-2-ethylenedioxybutane (4.5 g) as colourless needles, m.p. 61°–9° C.

Calculated for $C_{17}H_{20}O_3$: C, 74.97; H, 7.40%.
Found: C, 74.84 and 75.23; H, 7.55 and 7.45%.

EXAMPLE 2

4-(6'-Methoxy-2'-naphthyl)-2-ethoxybut-1-ene and 4-(6'-methoxy-2'-naphthyl)-2-ethoxybut-2-ene A solution of 4-(6'-methoxy-2'-naphthyl)butan-2-one (5 g), ethyl orthoformate (10 g) and ethanol (10 ml) was treated with dry, saturated ethereal hydrogen chloride (5 ml) and then left at room temperature overnight. Removal of the solvents and distillation of the product at 150°–60°/0.01 mm Hg gave a colourless oil, which was chromatographed on an alumina column using 10% ethereal petrol to afford a mixture of 4-(6'-methoxy-2'-naphthyl)-2-ethoxybut-1-ene and 4-(6'-methoxy-2'-naphthyl)-2-ethoxybut-2-ene.

EXAMPLE 3

4-(6'-Methoxy-2'-naphthyl)-2-acetoxybut-1-ene and 4-(6'-methoxy-2'-naphthyl)-2-acetoxybut-2-ene A mixture of 4-(6'-methoxy-2'-naphthyl)butan-2-one (5 g), isopropenyl acetate (250 g) and p-toluenesulphonic acid (0.5 g) was refluxed for 24 hours. The cooled solution was washed with water, dried and concentrated. The crude product was chromatographed on a silica gel column using 10% ethereal petrol to give a mixture of 4-(6'-methoxy-2'-naphthyl)-2-acetoxybut-1-ene and 4-(6'-methoxy-2'-naphthyl)-2-acetoxybut-2-ene (3.5 g).

What is claimed is:

1. An enol ether of the formula (II) or (III):

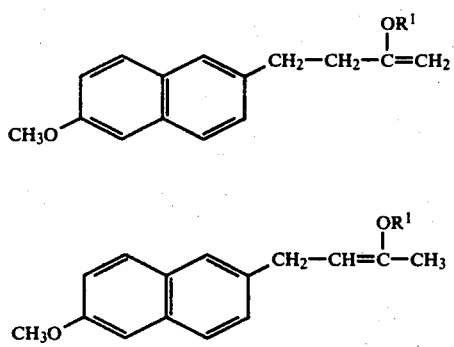

in each of which formulas $R^1$ is alkyl of 2–4 carbon atoms.

2. An enol ether of claim 1 of the formula (II):

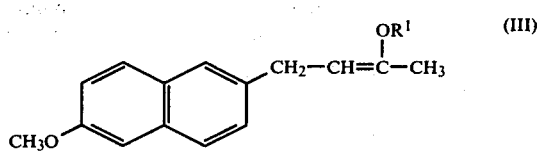

in which $R^1$ is alkyl of 2–4 carbon atoms.

3. An enol ether of claim 1 of the formula (III):

$$\text{(III)}$$

in which $R^1$ is alkyl of 2–4 carbon atoms.

4. An enol ether according to claim 1 in which $R^1$ is ethyl or propyl.

5. A pharmaceutical composition for treating inflammation which comprises an anti-inflammatory amount of an enol ether of claim 1 in combination with a pharmaceutically acceptable carrier.

6. A pharmaceutical composition for treating inflammation which comprises an anti-inflammatory amount of an enol ether of claim 2 in combination with a pharmaceutically acceptable carrier.

7. A pharmaceutical composition for treating inflammation which comprises an anti-inflammatory amount of an enol ether of claim 3 in combination with a pharmaceutically acceptable carrier.

8. A pharmaceutical composition for treating inflammation which comprises an anti-inflammatory amount of an enol ether of claim 4 in combination with a pharmaceutically acceptable carrier.

9. A pharmaceutical composition according to claim 5 in oral unit dosage form.

10. A method of treating inflammation which comprises administering an anti-inflammatory amount of a composition of claim 5.

11. A method according to claim 10 in which the administration is oral.

12. A method according to claim 10 in which the administration is oral and the composition is in unit dosage form.

* * * * *